United States Patent
Ju

(10) Patent No.: US 6,197,339 B1
(45) Date of Patent: *Mar. 6, 2001

(54) SUSTAINED RELEASE TABLET FORMULATION TO TREAT PARKINSON'S DISEASE

(75) Inventor: Tzu-chi Robert Ju, Portage, MI (US)

(73) Assignee: Pharmacia & Upjohn Company, Kalamazoo, MI (US)

( * ) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

(21) Appl. No.: 09/146,090

(22) Filed: Sep. 30, 1998

Related U.S. Application Data

(60) Provisional application No. 60/060,827, filed on Sep. 30, 1997.

(51) Int. Cl.[7] .......................... A61K 9/22; A61K 31/495; A61K 31/435
(52) U.S. Cl. .......................... 424/468; 424/464; 514/292; 514/233.2
(58) Field of Search ..................... 424/464, 468, 424/465, 451; 514/292, 233.2

(56) References Cited

U.S. PATENT DOCUMENTS

| | | | |
|---|---|---|---|
| 4,389,393 | 6/1983 | Schor et al. | 424/19 |
| 5,000,962 | 3/1991 | Sangekar et al. | 424/482 |
| 5,273,975 | 12/1993 | Moon et al. | 514/233 |

FOREIGN PATENT DOCUMENTS

| | | |
|---|---|---|
| 97/34932 | 9/1997 | (WO) . |
| 97/37639 | 10/1997 | (WO) . |

OTHER PUBLICATIONS

Dow's 1995 Formulating for Controlled Release Withe Methocel Premium Cellulose Ethers, Figure 24, p 21.
Dow's 1995 Formulating for Controlled Release Withe Methocel Premium Cellulose Ethers, Figure 20, p 20.
Heier et al., An Asymmetric Synthesis of (R)–5, 6–dihydro–5–(methylamino)–4H–imidazo–[4,5,1–ij]quinolin–2(1H)–one and its [2–14C]–and [6,7–3H2]–labeled forms, J. Labelled Compd. Radiopharm, 38(12), 1087–1098, 1996.*
Sethy et al., U–95666E: A Potential Anti–Parkinsonian Drug with Anxiolytic Activity, Prog. Neuro–Psychopharmacol. Biol. Psychiatry, 21(5), 873–883, 1997.*

* cited by examiner

Primary Examiner—Thurman K. Page
Assistant Examiner—Brian K. Seidleck
(74) Attorney, Agent, or Firm—Bruce Stein

(57) ABSTRACT

The sustained release tablet of (R)-5,6-dihydro-5-(methylamino)-4H-imidazo[4,5-ij]-quinolin-2(1H)-one (Z)-2-butenedioate (1:1) which is disclosed permits twice daily administration of (R)-5,6-dihydro-5-(methylamino)-4H-imidazo[4,5-ij]-quinolin-2(1H)-one (Z)-2-butenedioate (1:1) to treat humans with Parkinson's disease.

17 Claims, No Drawings

SUSTAINED RELEASE TABLET FORMULATION TO TREAT PARKINSON'S DISEASE

CROSS-REFERENCE TO RELATED APPLICATIONS

This application claims the benefit of U.S. provisional application Ser. No. 60/060,827 filed Sep. 30, 1997, under 35 USC §119(e)(i).

BACKGROUND OF THE INVENTION

1. Field of the Invention

The present invention is a pharmaceutical tablet formulation of (R)-5,6-dihydro-5-(methylamino)-4H-imidazo[4,5-ij]-quinolin-2(1H)-one (Z)-2-butenedioate (1:1) and a method of using it to treat Parkinson's disease.

2. Description of the Related Art

U.S. Pat. No. 5,273,975 generically claims (R)-5,6-dihydro-5-(methylamino)-4H-imidazo[4,5-ij]-quinolin-2(1H)-one (Z)-2-butenedioate (1:1), but does not disclosed it. It generically discloses that compounds are useful for treating Parkinson's disease.

U.S. Pat. No. 4,389,393 claims a sustained release pharmaceutical tablet formulation with less than 25.8% hydroxypropyl methylcellulose. Hydroxypropyl methylcellulose has been used extensively for producing sustained release (slow disintegration) tablet formulations.

U.S. Pat. No. 5,000,962 discloses a long acting tablet formulation which comprises more than 35 to 60% (by weight) of hydroxypropyl methylcellulose and lactose was used as an excipient. The present invention uses no lactose.

Dow's 1995 Formulating for Controlled Release With Methocel Premium Cellulose Ethers in FIG. 24 on page 21 discloses the use of starch with Methocel (hydroxypropyl methocellulose) for producing tablets containing theophylline. The tablets of the present invention do not contain theophylline but rather (R)-5,6-dihydro-5-(methylamino)-4H-imidazo[4,5-ij]-quinolin-2(1H)-one (Z)-2-butenedioate (1:1). FIG. 20 on page 20 discloses a relationship between tablet size and the percent released with lactose. Normally starch is used in an amount up to about 15–20% for immediate release tablet formulations. However, in sustained release formulations it is not used because it is preceived to promote disintergation. Dow discloses the use of starch (excipient) at an amount of 52.6%. The tablet formulation of the present invention uses starch in an amount of more than 60%.

International Publication WO97/34932 discloses pharmaceutical tablets containing mechanically damaged starch which provide delayed, controlled and targeted release formulations. The present invention does not use mechanically damaged starch.

International Publication WO97/37639 discloses a controlled-release pharmaceutical tablet containing cross-linked amylose and hydroxypropylmethylcellulose and 10–30% of hydroxypropyl methylcellulose. The tablet formulation of the present invention uses no cross-linked amylose and has from 30–40% hydroxypropyl methylcellulose.

SUMMARY OF INVENTION

Disclosed is a pharmaceutical composition which is a sustained release tablet for oral ingestion which comprises:

| | |
|---|---|
| (a) (R)-5,6-dihydro-5-(methylamino)-4H-imidazo[4,5-ij]-quinolin-2(1H)-one (Z)-2-butenedioate (1:1) | 0.3%–16% |
| (b) starch | 60%–69% |
| (c) hydroxypropyl methylcellulose | 30%–40% |

Further disclosed is a method of treating humans who have Parkinson's disease which comprises orally administering an anti-Parkinson's effective amount of (R)-5,6-dihydro-5-(methylamino)-4H-imidazo[4,5-ij]-quinolin-2(1H)-one (Z)-2-butenedioate (1:1).

DETAILED DESCRIPTION OF THE INVENTION (R)-5,6-dihydro-5-(methylamino)-4H-imidazo[4,5-ij]-quinolin-2(1H)-one (Z)-2-butenedioate (1:1) is made according to the process set forth in CHART A and in EXAMPLEs 1 thru 8.

It is preferred that (R)-5,6-dihydro-5-(methylamino)-4H-imidazo[4,5-ij]-quinolin-2(1H)-one (Z)-2-butenedioate (1:1) be administered as a capsule or tablet, more preferably a tablet. The tablet formulation contains the following components, the pharmacologically active ingredient, starch and hydroxypropyl methylcellulose.

The amount of the active ingredient, (R)-5,6-dihydro-5-(methylamino)-4H-imidazo[4,5-ij]-quinolin-2(1H)-one (Z)-2-butenedioate (1:1), per tablet is from about 0.3% (1 mg) to about 16% (56 mg) of (R)-5,6-dihydro-5-(methylamino)-4H-imidazo[4,5-ij]-quinolin-2(1H)-one (Z)-2-butenedioate (1:1); preferably from about 0.44% (1.5 mg) to about 10% (35 mg) of (R)-5,6-dihydro-5-(methylamino)-4H-imidazo[4,5-ij]-quinolin-2(1H)-one (Z)-2-butenedioate (1:1)/tablet. Note that 1 mg of (R)-5,6-dihydro-5-(methylamino)-4H-imidazo[4,5-ij]-quinolin-2(1H)-one (Z)-2-butenedioate salt is equivalent to about 0.63 mg of the free base, (R)-5,6-dihydro-5-(methylamino)-4H-imidazo[4,5-ij]-quinolin-2(1H)-one. It is preferred that the tablet be about 350 mg in total weight.

Many different starches are useful and can be used in place of each other or in combination with each other as mixtures. They include potato, corn, wheat, pregelatinized, sodium starch glycolate and equivalents thereof. It is preferred that the starch be either corn or pregelatinized starch, or a mixture thereof. The starch should be present in an amount of from about 60 to about 69%.

The hydroxypropyl methylcellulose should be present in an amount of from about 30 to about 40%. It is preferred that the hydroxypropyl methylcellulose be selected from the group consisting of hydroxypropyl methylcellulose 2208 USP 100 cps, hydroxypropyl methylcellulose 2208 USP 4,000 cps, hydroxypropyl methylcellulose 2208 USP 15,000 cps, hydroxypropyl methylcellulose 2208 USP 100,000 cps, hydroxypropyl methylcellulose 2910 USP 4,000 cps, hydroxypropyl methylcellulose 2910 USP 10,000 cps, or mixtures thereof. It is preferred that the hydroxypropyl methylcellulose be hydroxypropyl methylcellulose 2208 USP 4,000 cps or hydroxypropyl methylcellulose 2910 USP 4,000 cps. The hydroxypropyl methylcellulose can be any of the hydroxypropyl methylcelluloses individually or mixtures thereof.

It is preferable that the tablets contain magnesium stearate but it is not required. If magnesium stearate is present, it should be in an amount of from about 0.2 to about 2.0%.

It is preferable that the tablets contain colloidal silicon dioxide but it is not required. If colloidal silicon dioxide is present, it should be in an amount of from about 0.2 to about 1.0%.

As is known to those skilled in the art, other agents such as sweeteners, coloring agents, coatings, etc can be added to the tablet.

The tablet is made by either direct compression or wet granulation, both processes are well known to those skilled in the art. If the direct compression method is used, the active ingredient (R)-5,6-dihydro-5-(methylamino)-4H-imidazo[4,5-ij]-quinolin-2(1H)-one (Z)-2-butenedioate (1:1), the starch and the hydroxypropyl methylcellulose (and colloidal silicon dioxide, if used) are first individually screened and then mixed in an appropriate size container or blender. If magnesium stearate is used it also is screened and mixed with a portion of the material from the container or blender and then all the materials are thoroughly mixed. This lubricated mixture is compressed into tablets of desired weight and physical specifications by methods known to those skilled in the art.

If the wet granulation method is used, a binder solution is prepared using hydroxypropyl cellulose or povidone (PVP). The binder solution is sprayed into a mixture of the pharmaceutically active ingredient, (R)-5,6-dihydro-5-(methylamino)-4H-imidazo[4,5-ij]-quinolin-2(1H)-one (Z)-2-butenedioate (1:1) and a portion of the other ingredients except the lubricant (magnesium stearate). The wet granules should be dried in a dryer such as a fluidized bed. The dry mixture should then be mixed with the lubricant and the remaining ingredients to form the final mixture which is compressed into tablets of desired weight and physical specifications by methods known to those skilled in the art.

(R)-5,6-Dihydro-5-(methylamino)-4H-imidazo[4,5-ij]-quinolin-2(1H)-one (Z)-2-butenedioate (1:1) is used in the treatment of Parkinson's disease. It is administered twice a daily orally in the form of a tablet or capsule, preferably a tablet. Since Parkinson's disease is disease of the elderly and children are not involved, the drug is not expressed as mg/kg but rather as the amount per day. It is preferred that (R)-5, 6-dihydro-5-(methylamino)-4H-imidazo[4,5-ij]-quinolin-2 (1H)-one (Z)-2-butenedioate (1:1) be given in an amount of about 2 mg to about 112 mg/day, more preferably from about 3 mg to about 70 mg/day. It is preferred that the daily dose be divided into two equal amounts since the sustained release tablet formulation adequately maintains blood levels when administered twice daily.

The exact dosage and frequency of administration depends the severity of the condition being treated, the weight, general physical condition of the particular patient, other medication the individual may be taking as is well known to those skilled in the art and can be more accurately determined by measuring the blood level or concentration of the free base of (R)-5,6-dihydro-5-(methylamino)-4H-imidazo[4,5-ij]-quinolin-2(1H)-one (Z)-2-butenedioate (1:1) in the patient's blood and/or the patient's response to the particular condition being treated.

DEFINITIONS AND CONVENTIONS

The definitions and explanations below are for the terms as used throughout this entire document including both the specification and the claims.

DEFINITIONS

All temperatures are in degrees Centigrade.

TLC refers to thin-layer chromatography.

HPLC refers to high pressure liquid chromatography.

Saline refers to an aqueous saturated sodium chloride solution.

Chromatography (column and flash chromatography) refers to purification/separation of compounds expressed as (support; eluent). It is understood that the appropriate fractions are pooled and concentrated to give the desired compound(s).

IR refers to infrared spectroscopy.

NMR refers to nuclear (proton) magnetic resonance spectroscopy, chemical shifts are reported in ppm (δ) downfield from tetramethylsilane.

$[a]_D^{25}$ refers to the angle of rotation of plane polarized light (specific optical rotation) at 25° with the sodium D line (589A).

MS refers to mass spectrometry expressed as m/e, m/z or mass/charge unit. $[M+H]^+$ refers to the positive ion of a parent plus a hydrogen atom. EI refers to electron impact. CI refers to chemical ionization. FAB refers to fast atom bombardment.

Ether refers to diethylether.

Pharmaceutically acceptable refers to those properties and/or substances which are acceptable to the patient from a pharmacological/toxicological point of view and to the manufacturing pharmaceutical chemist from a physical/chemical point of view regarding composition, formulation, stability, patient acceptance and bioavailability.

When solvent pairs are used, the ratios of solvents used are volume/volume (v/v).

When the solubility of a solid in a solvent is used the ratio of the solid to the solvent is weight/volume (wt/v).

All reactions are run under a nitrogen atmosphere.

Melting points are uncorrected.

GLC conditions are as follows: Hewlett-Packard Model 5890A capillary gas chromatograph, J & W Scientific Inc., DB-5.5% phenylmethyl silicone column (15 m×0.53 mm×1.5 μm film thickness), helium carrier gas (100 ml/min.), hydrogen flame ionization detector. Programmed: 100°, 1 min; increasing 20°/min to 250°; 250°, 10 min.

HPLC conditions are as follows: Zorbax Rx-C8 column (4.6 mm×25 cm), solvent A—10% acetonitrile and 90% water (pH=3 phosphate buffer), solvent B—85% acetonitrile and 15% water (pH 3=phosphate buffer), programmed gradient: 90% A/10% B to 5% A/95% B over 12 minutes, maintain at 5% A/95% B for 4 to 10 minutes; λ=215 nm, flow=2 ml/min.

USP refers to United States Pharmacopeia.

cps refers to centiposes.

EXAMPLES

Without further elaboration, it is believed that one skilled in the art can, using the preceding description, practice the present invention to its fullest extent. The following detailed examples describe how to prepare the various compounds and/or perform the various processes of the invention and are to be construed as merely illustrative, and not limitations of the preceding disclosure in any way whatsoever. Those skilled in the art will promptly recognize appropriate variations from the procedures both as to reactants and as to reaction conditions and techniques.

EXAMPLE 1

(R)-2-(Methoxycarbonylamino)-3-phenylpropanoic acid (II)

A mixture of D-phenylalanine (I, 25.00 g, 0.151 mol) and sodium hydroxide (6.05 g, 0.151 mol) in water (170 ml) and tetrahydrofuran (225 ml) is cooled to −15°, and a mixture of methyl chloroformate (18.6 g, 0.197 mol) in tetrahydrofuran (50 ml) is added dropwise. When the one-half of the methyl chloroformate had been added, a mixture of sodium hydroxide (9.10 g, 0.227 mol) in water (20 ml) is added. When the addition is complete, the mixture is stirred at 25° for an additional 2 hours and acidified with hydrochloric acid (10%) to pH 2. The mixture is extracted twice with ether and the extracts are washed with saline and dried over magnesium sulfate. The solvent is removed under reduced pressure to give the title compound, NMR (CDCl$_3$) 3.09, 3.19, 3.65, 4.66, 5.25, 7.15–7.31 and 8.22 δ; IR (thin film) 1726, 1498, 1455, 1448 and 1377 cm$^{-1}$; MS calculated for $C_{11}H_{13}NO_4$= 224.0923, found=224.0921.

EXAMPLE 2

(R)-N-Methoxy-2-(methoxycarbonylamino)-3-phenylpropanamide (III)

A mixture of sodium carbonate (10.20 g, 96.2 mmol) in water (170 ml) is added to a mixture of (R)-2-(methoxycarbonylamino)-3-phenylpropanoic acid (II, EXAMPLE 1, ~0.148 mol crude) in methylene chloride. Methoxylamine hydrochloride (14.2 g, 0.170 mol) and 1-(3-dimethylaminopropyl)-3-ethylcarbodiimide hydrochloride (EDC) (31.21 g, 0.163 mol) are added, and the mixture is stirred at 20–25° for 22 hours. The mixture is diluted with tetrahydrofuran (to dissolve the precipitate) and the layers are separated. The aqueous layer is extracted with 1:1 tetrahydrofuran/ether, and the combined organic extracts are washed with hydrochloric acid (10%) and saturated sodium bicarbonate solution. The mixture is dried over magnesium sulfate, filtered and the solvent removed under reduced pressure. Crystallization from ethyl acetate gives the title compound, mp=154–155°; NMR (CDCl$_3$) 3.05, 3.58, 3.61, 4.34, 5.66, 7.15–7.31 and 9.44 δ; IR (mineral oil) 1694 and 1668 cm$^{-1}$; $[a]^{25}_D$=+5.2° (CH$_3$OH, c=1.045).

EXAMPLE 3

Methyl (R)-N-(1,2,3,4-Tetrahydro-1-methoxy-2-oxo-3-quinolinyl)-carbamate (IV)

A suspension of (R)-N-methoxy-2-(methoxycarbonylamino)-3-phenylpropanamide (III, EXAMPLE 2, 11.25 g, 44.6 mmol) in dichloromethane (170 ml) is cooled in an ice bath and trifluoroacetic acid (9.25 ml, 13.7 g, 0.120 mol) is added. Bis(trifluoroacetoxy)iodobenzene (19.78 g, 0.046 mol) is added portion wise over 10 min at 0°, and the mixture is stirred at this temperature for one hour. The mixture is washed with sodium carbonate mixture (10%) and dried over magnesium sulfate. The solvent is removed under reduced pressure to give a concentrate. Purification by flash chromatography (230–400 mesh silica gel, 40–50% ethyl acetate/hexane) gives the desired product. An analytical sample is crystallized from ethyl acetate/hexane to give the title compound, mp=117–119°; NMR (CDCl$_3$) 2.85, 3.44, 3.72, 3.93, 4.42, 5.82, 7.09, 7.33 and 7.22 δ; IR (mineral oil) 1722 and 1703 cm$^{-1}$; $[a]^{25}_D$=+34.20 (CH$_3$OH, c=0.927).

EXAMPLE 4

(R)-3-Methylamino-1,2,3,4-tetrahydroquinoline maleate (V)

A mixture of (R)-N-(1,2,3,4-tetrahydro-1-methoxy-2-oxo-3-quinolinyl)carbamate (IV, EXAMPLE 3, 29.1 g, 116.4 mmol) in dry tetrahydrofuran (400 ml) is cooled to 0° and borane methylsulfide (10.0 M solution, 70 ml, 6.0 eq) is slowly added. The mixture is allowed to warm to 25° and stirred or 2.5 hours. The mixture is then refluxed on a steam bath for 30 hours and then cooled to 0°, quenching dropwise (careful—hydrogen evolution) with hydrochloric acid (10%, 160 ml). This mixture is refluxed on the steam bath for 1.5 hours, cooled in ice, and made basic with aqueous sodium hydroxide (12 N). The mixture is extracted twice with ether and the combined extracts are washed with saline and dried over magnesium sulfate. The solvent is removed under reduced pressure to a concentrate which is carried on without further purification. Examination of crude diamine (V) by GLC shows peaks at 5.15 min (2%), 5.46 min (V, 85%), 5.83 min (3%) and 7.39 min (10%). To obtain an analytical sample, an aliquot of crude (V) is crystallized as its maleate salt in methanol/ether, mp=175°; NMR of the maleic acid salt (CDCl$_3$) 2.64, 2.80, 3.11, 3.20–3.52, 3.55, 5.92, 6.03, 6.53–6.58, 6.927–6.97 and 8.48 δ; $[a]^{25}_D$=+19.0° (CH$_3$OH, c=1.01); IR (thin film) 1638 and 1608 cm$^{-1}$.

EXAMPLE 5

(R)-Methyl-(1,2,3,4-tetrahydro-3-quinolinyl) carbamic acid, phenylmethyl ester (VI)

A mixture of (R)-1,2,3,4-tetrahydro-N-methyl-3-quinolinamine of crude material prepared above (V, EXAMPLE 4, 15.0 g), approximately 84.4 mmol) in toluene (50 ml) is stirred at −40° while N-(benzyloxycarbonyloxy)succinimide (24.2 g, 97.1 mmol) in toluene (150 ml) is added over one hr. After 30 min at −40°, GLC analysis indicated that all of (V) had been consumed. The mixture is quenched by the addition of sodium bicarbonate (10% aqueous solution, 300 ml) and warmed to 0°, followed by the addition of methanol (100 ml). This is stirred overnight and then extracted with ethyl acetate. Drying over magnesium sulfate and solvent removal gives a liquid which is purified by flash chromatography (230–400 mesh silica gel; hexane/ethyl acetate, 4/1) which crystallized from ethyl acetate/hexane to give the title compound, mp=80°; NMR (CDCl$_3$) 2.88, 2.80–3.04, 3.30, 3.83, 4.57, 5.16, 6.51, 6.64, 6.96–7.02 and 7.35 δ; $[a]^{25}_D$=−50.1° (CH$_3$OH, c=0.816); IR (mineral oil) 1680 and 1606 cm$^{-1}$.

EXAMPLE 6

(R)-Methyl-[ 1,2,3,4-tetrahydro-1-[(methoxyamino)carbonyl]-3-quinolinyl]carbamic acid, phenylmethyl ester (VII)

A mixture of (R)-methyl-(1,2,3,4-tetrahydro-3-quinolinyl)carbamic acid, phenylmethyl ester (VI, EXAMPLE 5, 3.81 g, 12.86 mmol) and triethylamine (3.9 g, 39 mmol) in dry tetrahydrofuran (50 ml) is added with stirring to a mixture of phosgene (7.1 ml of a 1.93 M toluene solution) in tetrahydrofuran (100 ml) at 0°. After one hour, methoxylamine hydrochloride (2.15 g, 25.7 mmol) and triethylamine (3.9 g, 39 mmol) are added, and the mixture is stirred at 20–25° for two days. The 15 mixture is diluted with ether and washed with water and saline. The organic layer is dried over magnesium sulfate and the solvent is removed under reduced pressure. The residue is sufficiently pure for the next step. An analytical sample is purified via flash chromatography (230–400 mesh silica gel; ethyl acetate/hexane, 50/50) to give the title compound, NMR (CDCl$_3$) 2.88, 2.77–2.97, 3.75, 3.52–4.08, 4.54, 5.13, 7.10–7.27, 7.35 and 7.76 δ; IR (thin film) 1734, 1697 and 1605 cm$^{-1}$; $[a]^{25}_D$=+38° (CH$_3$OH, c=0.980); MS calculated for $C_{20}H_{23}N_3O_4$=369.1688, found=369.1682.

EXAMPLE 7

(R)-Methyl-(1,2,5,6-tetrahydro-1-methoxy-2-oxo-4H-imidazo[4,5,1-ij]quinolinyl-5-yl)carbamic acid, phenylmethyl ester (VIII)

A mixture of (R)-methyl-[1,2,3,4-tetrahydro-1-[(methoxyamino)carbonyl]-3-quinolinyl]carbamic acid, phenylmethyl ester (VII, EXAMPLE 6, 7.26 g, 19.7 mmol) in chloroform (150 ml) is cooled to −5° in an ice-salt bath. Bis(trifluoroacetoxy)iodobenzene (10.14 g, 23.6 mmol) is added, and the mixture is stirred at −5 to 0° for four hours and then at 20–25° for two more hours at which time the reaction is complete by TLC. The reaction mixture is washed with 10% aqueous sodium carbonate, back-extracting the aqueous fractions with ether. The combined organic layers are dried over magnesium sulfate, and the solvent removed under reduced pressure to a concentrate. Purification of the concentrate by flash chromatography (230–400 mesh silica gel; ethyl acetate/hexane, 50/50) gives the 35 product. HPLC analysis indicated two peaks, 10.79 min (97.4%) and 11.95 min (2.6%). An analytical sample (0.54 g) is crystallized from ethyl acetate/hexane to give the title compound, mp=105–106.5°; NMR (CDCl$_3$) 2.93, 2.90–3.30, 3.14, 3.68, 4.07, 4.11, 4.65, 5.16, 6.88, 6.96, 7.04 and 7.36 δ; IR (mineral oil): 1725, 1717 and 1694 cm$^{-1}$; $[a]^{25}_D$=+46.8° (CH$_3$OH, c=0.731).

EXAMPLE 8

(R)-5,6-Dihydro-5-(methylamino)-4H-imidazo[4,5,1-ij]quinolin-2(1H)-one maleate (IX)

A mixture of methyl-(1,2,5,6-tetrahydro-1-methoxy-2-oxo-4H-imidazo[4,5,1-ij]quinolinyl-5-yl)carbamic acid phenylmethyl ester (VIII, EXAMPLE 7, 3.87 g, 10.5 mmol) and 20% palladium hydroxide on carbon (1.0 g) in absolute ethanol (100 ml) is shaken in a Parr apparatus with an initial hydrogen pressure of 50 psi for 19 hours. The mixture is filtered through diatomaceous earth, and the catalyst is washed with ethanol, and the solvent is removed under reduced pressure. The concentrate is dissolved in methanol (25 ml) and added to a mixture of maleic acid (1.20 g, 10.3 mmol) in methanol (25 ml). Crystallization gives the desired product, mp=211°. A second crop is obtained by adding ether (0.29 g). HPLC analysis of the title compound indicates it to be greater than 99% pure; NMR of the maleic acid salt (DMSO) 2.68, 3.05, 3.22, 3.90–4.06, 6.05, 6.85–6.97, 8.74 and 10.83 δ; IR (mineral oil) 1696 and 1638 cm$^{-1}$; $[a]^{25}_D$=−26.3° (H$_2$O, c=0.836).

EXAMPLE 9

Tablet—35% Hydroxypropyl Methylcellulose 2208 USP 4,000 cps—350 mg Tablet

| | |
|---|---|
| (R)-5,6-dihydro-5-(methylamino)-4H-imidazo[4,5-ij]-quinolin-2(1H)-one (Z)-2-butenedioate (1:1) | 3.97 mg (1.1%) |
| Pregelatinized Starch | 220.38 mg (62.8%) |
| Hydroxypropyl Methylcellulose 2208 USP 4,000 cps | 122.50 mg (35.0%) |
| Colloidal Silicon Dioxide | 1.40 mg (0.4%) |
| Magnesium Stearate | 1.75 mg (0.5%) |
| Total Tablet Weight | 350.00 mg (100%) |

The tablet is prepared by dry granulation as follows. The pharmaceutically active ingredient, (R)-5,6-dihydro-5-(methylamino)-4H-imidazo[4,5-ij]-quinolin-2(1H)-one (Z)-2-butenedioate (1:1), the starch, the hydroxypropyl methylcellulose and the colloidal silicon dioxide are individually screened and then mixed in an appropriate size container or blender. The magnesium stearate is screened and mixed with a portion of the material from the container or blender and then all the materials are thoroughly mixed. This lubricated mixture is compressed into 350 mg tablets of desired physical specifications.

EXAMPLE 10

Tablet—35% Hydroxypropyl Methylcellulose 2910 USP 4,000 cps—350 mg Tablet

| | |
|---|---|
| (R)-5,6-dihydro-5-(methylamino)-4H-imidazo[4,5-ij]-quinolin-2(1H)-one (Z)-2-butenedioate (1:1) | 3.97 mg |
| Pregelatinized Starch | 220.38 mg |
| Hydroxypropyl Methylcellulose 2910 USP 4,000 cps | 122.50 mg |
| Colloidal Silicon Dioxide | 1.40 mg |
| Magnesium Stearate | 1.75 mg |
| Total Tablet Weight | 350.00 mg |

Following the general procedure of EXAMPLE 9 and making non-critical variations the tablet formulation of EXAMPLE 10 is prepared.

EXAMPLE 11

Tablet—35% Hydroxypropyl Methylcellulose 2910 USP 4,000 cps—350 mg Tablet; Corn Starch

| | |
|---|---|
| (R)-5,6-dihydro-5-(methylamino)-4H-imidazo[4,5-ij]-quinolin-2(1H)-one (Z)-2-butenedioate (1:1) | 3.97 mg |
| Corn Starch | 220.38 mg |
| Hydroxypropyl Methylcellulose 2910 USP 4,000 cps | 122.50 mg |
| Colloidal Silicon Dioxide | 1.40 mg |
| Magnesium Stearate | 1.75 mg |
| Total Tablet Weight | 350.00 mg |

Following the general procedure of EXAMPLE 9 and making non-critical variations the tablet formulation of EXAMPLE 11 is prepared.

CHART A

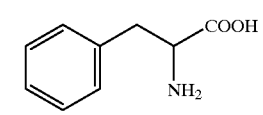

(I)

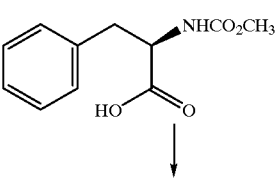

(II)

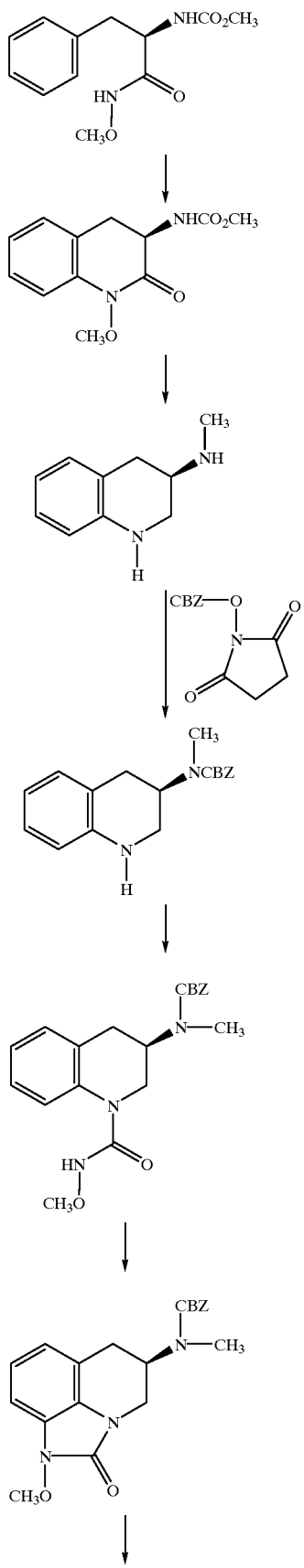

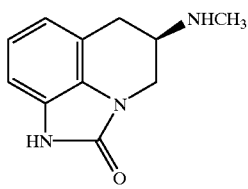

What is claimed is:

1. A pharmaceutical composition which is a sustained release tablet for oral ingestion which comprises:

| | |
|---|---|
| (a) (R)-5,6-dihydro-5-(methylamino)-4H-imidazo[4,5-ij]-quinolin-2(1H)-one (Z)-2-butenedioate (1:1) | 0.3%–16% |
| (b) starch | 60%–69% |
| (c) hydroxypropyl methylcellulose | 30%–40% |

2. A pharmaceutical composition which is a substained release tablet for oral ingestion which comprises:

| | |
|---|---|
| (a) (R)-5,6-dihydro-5-(methylamino)4H-imidazo[4,5-ij]-quinolin-2(1H)-one (Z)-2-butenedioate (1:1) | 0.44%–10% |
| (b) pregelatinized or corn starch | 60%–67% |
| (c) hydroxypropyl methylcellulose | 30%–40% |

3. A pharmaceutical composition according to claim 1 where (R)-5,6-dihydro-5-(methylamino)-4H-imidazo[4,5-ij]-quinolin-2(1H)-one (Z)-2-butenedioate (1:1) is present in an amount from about 0.3% (1 mg) to about 16% (56 mg)/tablet.

4. A pharmaceutical composition according to claim 1 where (R)-5,6-dihydro-5-(methylamino)-4H-imidazo[4,5-ij]-quinolin-2(1 H)-one (Z)-2-butenedioate (1:1) is present in an amount of about 0.44% (1.5 mg), 0.88% (3.1 mg), 1.76% (6.2 mg), 3.52% (12.3 mg) and 5.33% (19 mg)/tablet.

5. A pharmaceutical composition according to claim 1 where the starch is pregelatinized or corn starch.

6. A pharmaceutical composition according to claim 1 where the starch is a mixture of pregelatinized and corn starch.

7. A pharmaceutical composition according to claim 1 where the hydroxypropyl methylcellulose is selected from the group consisting of hydroxypropyl methylcellulose 2208 USP 100 cps,
hydroxypropyl methylcellulose 2208 USP 4,000 cps,
hydroxypropyl methylcellulose 2208 USP 15,000 cps,
hydroxypropyl methylcellulose 2208 USP 100,000 cps,
hydroxypropyl methylcellulose 2910 USP 4,000 cps,
hydroxypropyl methylcellulose 2910 USP 10,000 cps,
or mixtures thereof.

8. A pharmaceutical composition according to claim 7 where the hydroxypropyl methylcellulose is hydroxypropyl methylcellulose 2208 USP 4,000 cps or hydroxypropyl methylcellulose 2910 USP 4,000 cps.

9. A pharmaceutical composition according to claim 1 which contains magnesium stearate.

10. A pharmaceutical composition according to claim 9 where the magnesium stearate is present in an amount of from about 0.2 to about 2.0%.

11. A pharmaceutical composition according to claim 1 which contains colloidal silicon dioxide.

12. A pharmaceutical composition according to claim 11 where the colloidal silicon dioxide is present in an amount of from about 0.2 to about 1.0%.

13. A pharmaceutical composition according to claim 1 where the tablet is about 350 mg in total weight.

14. A method of treating humans who have Parkinson's disease according to claim 1 which comprises orally administering an anti-Parkinson's effective amount of (R)-5,6-dihydro-5-(methylamino)-4H-imidazo[4,5-ij]-quinolin-2(1H)-one (Z)-2-butenedioate (1:1).

15. A method of treating humans who have Parkinson's disease according to claim 14 where the (R)-5,6-dihydro-5-(methylamino)-4H-imidazo[4,5-ij]-quinolin-2(1H)-one (Z)-2-butenedioate (1:1) is administered twice daily.

16. A method of treating humans who have Parkinson's disease according to claim 14 where the effective amount is from about 2 mg to about 112 mg/day.

17. A method of treating humans who have Parkinson's disease according to claim 16 where the effective amount is from about 3 mg to about 70 mg/day.

* * * * *

UNITED STATES PATENT AND TRADEMARK OFFICE
CERTIFICATE OF CORRECTION

PATENT NO. : 6,197,339 B1
DATED : March 6, 2001
INVENTOR(S) : Tzu-chi Robert Ju

It is certified that error appears in the above-identified patent and that said Letters Patent is hereby corrected as shown below:

Title page,
Column 1,
"[22] Filed: Sept. 30, 1998" should read -- [22] Filed: 09/03/98 --

Signed and Sealed this

Thirtieth Day of October, 2001

Attest:

NICHOLAS P. GODICI
Attesting Officer
Acting Director of the United States Patent and Trademark Office